US007429470B2

(12) United States Patent
Lee et al.

(10) Patent No.: US 7,429,470 B2
(45) Date of Patent: Sep. 30, 2008

(54) METHOD FOR PURIFICATION OF NUCLEIC ACIDS BY PHASE SEPARATION USING LASER AND BEADS

(75) Inventors: Jeong-gun Lee, Seoul (KR); Young-nam Kwon, Gyeonggi-do (KR); Young-a Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/265,461

(22) Filed: Nov. 2, 2005

(65) Prior Publication Data
US 2006/0094051 A1   May 4, 2006

(30) Foreign Application Priority Data
Nov. 3, 2004   (KR) ............... 10-2004-0088907

(51) Int. Cl.
*C12N 13/00* (2006.01)
*C12N 1/08* (2006.01)
*G01N 33/00* (2006.01)
*C07H 21/02* (2006.01)

(52) U.S. Cl. .............. 435/173.1; 435/270; 436/94; 536/23.1

(58) Field of Classification Search ............ 435/6, 435/173.1, 270; 436/94; 536/23.1
See application file for complete search history.

(56) References Cited

U.S. PATENT DOCUMENTS

| 5,234,809 | A | | 8/1993 | Boom et al. |
| 5,403,710 | A | * | 4/1995 | Weisburg et al. ........... 435/6 |
| 5,705,628 | A | | 1/1998 | Hawkins |
| 6,156,576 | A | | 12/2000 | Allbritton et al. ........ 436/63 |
| 6,335,201 | B1 | * | 1/2002 | Allbritton et al. ........ 436/63 |
| 6,613,525 | B2 | | 9/2003 | Nelson et al. |
| 6,685,730 | B2 | | 2/2004 | West et al. |
| 7,192,560 | B2 | | 3/2007 | Parthasarathy et al. |
| 2003/0095897 | A1 | | 5/2003 | Grate et al. |
| 2003/0096429 | A1 | * | 5/2003 | Baeumner et al. ......... 436/174 |
| 2006/0188876 | A1 | * | 8/2006 | Kilaas et al. ............. 435/6 |

FOREIGN PATENT DOCUMENTS

EP   1 650 297 A2   4/2006

OTHER PUBLICATIONS

Deggerdal, Arne and Larsen, Frank, "Rapid Isolation of PCR-Ready DNA from Blood, Bone Marrow and Cultured Cells, Based on Paramagnetic Beads," *Bio Techniques* (1997) 22(3): 554-557.
Li, Huaina et al, "Spatial Control of Cellular Measurements with the Laser Micropipet," *Anal. Chem.* (2001) 73: 4625-4631.
Rudi, K. et al., "Rapid, Universal Method of Isolate PCR-Ready DNA Using Magnetic Beads," *BioTechniques*, (1997) 22: 506-511.
Taylor, Michael T. et al., "Lysing Bacterial Spores by Sonication through a Flexible Interface in a Microfluidic System," *Anal. Chem.* (2001) 73: 492-496.
European Search Report; Application No. EP 05 02 4014; Date: Jun. 14, 2006.
"Recent Developments of Magnetic Beads for Use in Nucleic Acid Purification"; Authors: Peter R. Levison, Stephen E. Badger, Jon Dennis, Prit Hathi, Martin J. Davies, Ian J. Bruce, Dieter Schimkat; Journal of Chromatography A. 816 (1998) 107-111.
"Quantitative Cell Lysis of Indigenous Microorganisms and Rapid Extracton of Microbial DNA from Sediment"; Authors: Margret I. More, James b. Herrick, Margarida C. Silva, William C. Ghiorse, and Eugene L. Madsen; XP 000574303; Applied and Environmental Microbiology, May 1994, p. 1572-1580.
Laser Based Disruption of *Bacillus* Spores on a Microchip; Authors: Oliver Hofmann, Kirk Murray, Alan-Shaun Wilkinson, Timothy Cox, Andreas Manz Micro Total Analysis Systems 2004, vol. 2, XP009066976; Sep. 26-30, 2004.
Elgort, M.G., et al.; "Extraction and Amplification of Genomic DNA from Human Blood on Nanoporous Aluminum Oxide Membranes"; Clinical Chemistry; vol. 50, No. 10; pp. 1817-1819; 2004.
Li, H., et al.; "Selective genotyping of individual cells by capillary polymerase chain reaction"; Electrophoresis; vol. 23; pp. 3372-3380; 2002.
Tian, H., et al.; "Evaluation of Silica Resins for Direct and Efficient Extraction of DNA from Complex Biological Matrices in a Miniaturized Format"; Analytical Biochemistry; vol. 283; pp. 175-191; 2000.
Safarik, I., et al.; "Biologically Active Compounds and Xenobiotics: Magnetic Affinity Separations"; Encyclopedia of Separation Science, Academic Press; pp. 2163-2170; 2000.
Liu, R.H., et al.; "Self-Contained, Fully Integrated Biochip for Sample Preparation, Polymerase Chain Reaction Amplification, and DNA Microarray Detection"; Anal. Chem.; vol. 76; pp. 1824-1831; 2004.

* cited by examiner

*Primary Examiner*—Bradley L Sisson
(74) *Attorney, Agent, or Firm*—Cantor Colburn LLP (57) ABSTRACT

An apparatus and method for purification of nucleic acids of cells or viruses are provided. The nucleic acid purification apparatus includes: a cell lysis capillary having a sample inlet through which samples and magnetic beads are introduced; a vibrator attached to the capillary and mixing the samples and the magnetic beads in the capillary; a laser generator attached to the capillary and supplying a laser to the capillary; and a magnetic force generator attached to the capillary and fixing the magnetic beads to a capillary wall. According to the method and apparatus, PCR yield can be increased since PCR inhibitors can be readily removed by means of a phase separation in a capillary. The use of an electromagnet ensures the removal of the PCR inhibitors. In addition, since cell lysis and DNA purification process can be simultaneously performed, LOC steps can be reduced.

13 Claims, 7 Drawing Sheets

METHOD FOR PURIFICATION OF NUCLEIC ACIDS BY PHASE SEPARATION USING LASER AND BEADS

BACKGROUND OF THE INVENTION

This application claims the benefit of Korean Patent Application No. 10-2004-0088907, filed on Nov. 3, 2004, in the Korean Intellectual Property Office, the disclosure of which is incorporated herein in its entirety by reference.

1. Field of the Invention

The present invention relates to an apparatus and method for purification of nucleic acids by phase separation using a laser and beads.

2. Description of the Related Art

An efficient extraction of DNA from cells is necessary for many applications and is essential for molecular diagnostics, specifically for pathogen identification and quantification. Molecular diagnostics is generally performed by DNA amplification after DNA extraction steps. DNA amplification reactions include polymerase chain reaction (PCR), ligase chain reaction, stranded-displacement amplification, nucleic acid-based amplification, repair chain reaction, helicase chain reaction, QB replicase amplification, ligation activated transcription.

Isolation methods of DNA from cells were provided using materials that have the proclivity of binding DNA. Example materials of isolation methods of DNA are silica, glass fiber, anion exchange resins and magnetic beads (Rudi, K. et al., *Biotechniqures* 22, 506-511 (1997); and Deggerdal, A. et al., *Biotechniqures* 22, 554-557 (1997)). To avoid the manual steps and to remove operator error, several automatic machines were developed for high-throughput DNA extraction.

Cell lysis is conventionally performed by mechanical, chemical, thermal, electrical, ultrasonic and microwave method (Michael T. Taylor et al., *Anal.Chem.*, 73, 492-496 (2001)).

Laser has many advantages for disruption of cells and highly applicable to Lab-On-a-Chip (LOC) (Huaina Li et al., *Anal Chem*, 73, 4625-4631 (2001)).

U.S. Patent Publication No. 2003/96429 A1 discloses a laser-induced cell lysis system. When only a laser is used, an efficient cell lysis does not occur. As a result of performing an experiment using *E. coli* placed in a very clear solution, it is confirmed that when irradiating only a laser, a low cell lysis efficiency is obtained. A concentration of DNA measured after irradiating a laser for 150 seconds is 3.77 ng/µl because the laser energy is not efficiently transferred to the cells. A concentration of DNA measured after boiling cells at 95° C. for 5 minutes by means of a conventional heating method is 6.15 ng/µl.

U.S. Pat. No. 6,685,730 discloses optically-absorbing nanoparticles for enhanced tissue repair. This patent includes a method of joining tissue comprising: delivering nanoparticles having dimensions of from 1 to 1000 nanometers that absorb light at one or more wavelengths to the tissue to be joined; and exposing said nanoparticles to light at one or more wavelengths that are absorbed by the nanoparticles. This method causes only a loss of function of cells by using a laser and nanoparticles and there is no description of a method of disrupting cells by vibrating a solution containing cells and particles.

Conventionally, a method of purifying nucleic acids using a solid phase is known. For example, U.S. Pat. No. 5,234,809 discloses a method of purifying nucleic acids using a nucleic acid binding solid phase. Specifically, the method includes mixing a starting material, a chaotropic material and a nucleic acid binding solid phase, separating the solid phase with the nucleic acid bound thereto from the liquid, and washing the solid phase nucleic acid complexes.

However, this method is time consuming and complicated, and thus is not suitable for LOC. The method also has a problem of the use of the chaotropic material. That is, when the chaotropic material is not used, nucleic acids are not bound to the solid phase. The chaotropic material is harmful to humans, and thus should be handled with caution. Also, the chaotropic material acts as a material disturbing the subsequent step, and thus should be removed from purified nucleic acids during or after purification.

For the purpose of LOC implementation, the entire step of DNA isolation should be reduced and it is necessary to perform the PCR directly after cell lysis. To perform the PCR directly after cell lysis, the concentration of the resulting PCR inhibitors after cell lysis should be reduced. Thus, a method of removing the PCR inhibitors while performing cell lysis for the purpose of LOC implementation is required.

Thus, the inventors of the present invention researched for a method to overcome the above problems and discovered that nucleic acids can be effectively purified when cells or viruses are disrupted by vibrating a solution containing them using micro magnetic beads and a laser, the resulting PCR inhibitors attach to the magnetic beads, and then the magnetic beads to which the PCR inhibitors are attached are removed with a magnet attached to a capillary-shaped container wall.

SUMMARY OF THE INVENTION

The present invention provides an apparatus and method for effective purification of nucleic acids by phase separation using a laser and beads.

According to an aspect of the present invention, there is provided a nucleic acid purification apparatus of cells or viruses including: a cell lysis capillary having a sample inlet through which samples and magnetic beads are introduced and performing phase separation; a vibrator attached to the capillary and mixing the samples and the magnetic beads in the capillary; a laser generator attached to the capillary and supplying a laser to the capillary; and a magnetic force generator attached to the capillary and fixing the magnetic beads to a capillary wall.

In the apparatus, in the cell lysis capillary, samples and magnetic beads injected through a sample inlet are mixed and cell lysis is performed when a laser beam is irradiated thereto. The vibrator is a device for mixing samples and magnetic beads in the cell lysis capillary and can be any device capable of generating vibration. The laser generator is a device for supplying a laser beam to the cell lysis capillary and can emit laser beam with a specific wavelength or light with two or more wavelengths. The magnetic beads are boiled by the laser energy.

In the apparatus, the vibrator can include sonicators, vibrators using a magnetic field, vibrators using an electric field, mechanical vibrators such as a vortex etc., and piezoelectric materials.

In the apparatus, the magnetic force generator is located above a laser pathway and may be an electromagnet which is turned on when the magnetic beads in the cell lysis capillary are boiled.

The apparatus may further include a DNA amplification chamber connected to the cell lysis capillary through a channel which is opened or closed by a valve.

In the apparatus, the cell lysis capillary refers to a container having a capillary shape.

According to another aspect of the present invention, there is provided a method of purifying nucleic acids using the nucleic acid purification apparatus, the method including: injecting a solution containing cells or viruses in a capillary-shaped container containing magnetic beads; vibrating the magnetic beads; irradiating a laser beam onto the magnetic beads to disrupt the cells or viruses and binding compounds in the resulting cell or virus lysate to the magnetic beads; fixing the magnetic beads, to which the compounds in the cell or virus lysate are bound, to a capillary-shaped container wall by means of a magnetic force generator; and obtaining a solution without the magnetic bead.

According to another aspect of the present invention, there is provided a method of continuously performing a purification and amplification of the nucleic acids using the nucleic acid purification apparatus, the method including: injecting a solution containing cells or viruses to a capillary-shaped container containing magnetic beads; vibrating the magnetic beads; irradiating a laser beam onto the magnetic beads to disrupt the cells or viruses and binding compounds in the resulting cell or virus lysate to the magnetic beads; fixing the magnetic beads, to which the compounds in the cell or virus lysate are bound, to a capillary-shaped container wall by means of a magnetic force generator; and obtaining a solution without the magnetic bead and transferring the resulting solution to a amplification chamber through a channel connecting the container and the amplification chamber to perform amplification.

In the method, the laser may include a pulse laser or continuous wave (CW) laser.

In the method, the pulse laser may be 1 mJ/pulse or more and the CW laser may have a power of 10 mW or more. In an embodiment of the method, the pulse laser is 32 mJ/pulse or more and the CW laser has a power of 10 W or more.

In the method, the laser may be generated at a wavelength of 400 nm or more. In an embodiment of the method, the laser is generated at a wavelength from 750 nm to 1300 nm. The laser may be generated in one or more wavelength ranges.

In the method, the size of the magnetic beads may be from 50 nm to 1,000 µm. In an embodiment of the method, the size of the magnetic beads is 1-50 µm. The magnetic beads may be a mixture of beads having two or more sizes.

In the method, the container may have a ratio of diameter to length ranging from 1:2 to 1:50 and have a diameter ranging from 1 nm to 5 mm.

In the method, the container may be selected from the group consisting of polymers, organic materials, silicon, glass and metals.

In the method, the magnetic beads may include at least one material selected from the group consisting of ferromagnetic Fe, Ni, Cr, and oxides thereof.

In the method, the magnetic beads may be polymers, organic materials, silicon or glass coated with a ferromagnetic metal.

In the method, the magnetic beads may have a negatively-charged surface.

In the method, the solution can be selected from the group consisting of saliva, urine, blood, serum and cell cultures.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail.

The present invention relates to a nucleic acid purification apparatus of cells or viruses including: a cell lysis capillary having a sample inlet through which samples and magnetic beads are introduced; a vibrator attached to the capillary and mixing the samples and the magnetic beads in the capillary; a laser generator attached to the capillary and supplying a laser to the capillary; and a magnetic force generator attached to the capillary and fixing the magnetic beads to a capillary wall.

Figure 1:
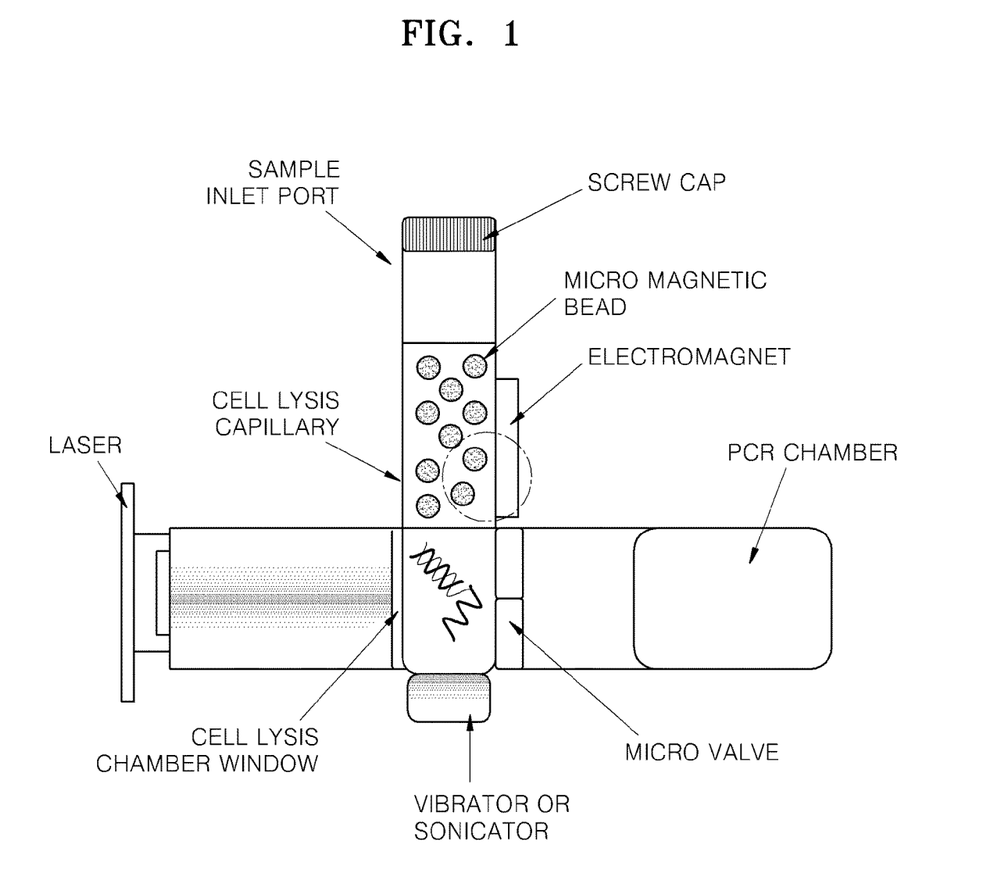
FIG. 1 is a schematic diagram of an embodiment of a system used to separate a micro magnetic bead phase and a DNA solution phase after cell lysis using micro magnetic beads and a laser.

FIG. 1 is a schematic diagram of an embodiment of a system used to separate a micro magnetic bead phase and a DNA solution phase after cell lysis using micro magnetic beads and a laser. Samples and magnetic beads are injected to a cell lysis capillary through a sample inlet, and then are mixed by a vibrator. When a laser beam is irradiated onto the mixture under vibration, the magnetic beads exposed to the laser convert light energy into heat by laser ablation. The magnetic beads heated by the laser beam are boiled and PCR inhibitors, such as proteins and cell debris denatured by boiling, are attached to the magnetic beads. The magnetic beads with the PCR inhibitors attached thereto are attached to a capillary wall. Thus, a phase separation between a DNA containing solution located at the lower portion of the capillary and most magnetic beads attached to the capillary wall, located at the upper portion of the capillary, is occurred. The DNA containing solution phase separated at the lower portion of the capillary is transferred to a polymerase chain reaction (PCR) chamber to perform a PCR. This transferring can be performed by a pump using electric, mechanic force, and the like.

A cell lysis capillary can be composed of a material which the laser can sufficiently pass through or have a window of such a material. The phase containing the separated beads non-specifically binds to the glass wall, which occurs more effectively in a capillary with a limited diameter. A fixed electromagnet or permanent magnet can be used to ensure the fixation of the separated phases and designate fixing regions.

In an embodiment of the present invention, the vibrator can includes sonicators, vibrators using magnetic field, vibrators using electric field, mechanical vibrators such as a vortex etc., or piezoelectric materials. The vibrator is attached to the cell lysis capillary and can be any device capable of vibrating the mixed solution of the cells and the micro magnetic beads.

In an embodiment of the present invention, the magnetic force generator is located above a laser pathway and is preferably an electromagnet that is turned on when the magnetic beads in the cell lysis capillary are boiled. As illustrated in FIG. 1, the electromagnet should be located above the laser pathway because if it is located within the laser pathway, the magnetic beads become attached to the electromagnet before they adsorb the PCR inhibitors, thereby resulting in a reduction in the effects of adsorbing the PCR inhibitors. An electromagnet that is turned on when the magnetic beads in the cell lysis capillary are boiled is preferable. Although an electromagnetic is turned on before the magnetic beads are boiled, the magnetic force does not influence the magnetic beads due to the spatial separation of the magnetic bead and the electromagnet so that the magnetic beads cannot be attached to the electromagnet. In addition, the beads should be magnetized in order to be removed by the electromagnet.

In an embodiment of the present invention, the nucleic acid purification apparatus can further include a DNA amplification chamber connected to the cell lysis capillary through a channel which is opened or closed by a valve. For the purpose of the LOC implementation, an amplification system of the purified DNA is necessary. The purified DNA can be detected using a spectrophotometer, micro magnetic beads, an electrochemical method, electrochemiluminescence, radiation and fluorescent label, a real-time PCR method, and the like. The PCR method is most suitable to sufficiently amplify a desired DNA. Other DNA amplification methods can also be applied and direct detection through the real-time PCR method, etc. is also possible.

In an embodiment of the present invention, the cell lysis capillary has preferably a diameter-to-length ratio ranging from 1:2 to 1:50 and has preferably a diameter ranging from 1 nm to 5 mm.

The present invention also relates to a method of purifying nucleic acids using the nucleic acid purification apparatus, the method including: injecting a solution containing cells or viruses to a capillary-shaped container containing magnetic beads; vibrating the magnetic beads; irradiating a laser beam onto the magnetic beads to disrupt the cells or viruses and binding compounds in the resulting cell or virus lysate to the magnetic beads; fixing the magnetic beads, to which the compounds in the cell or virus lysate are bound, to a capillary-shaped container wall by means of a magnetic force generator; and obtaining a solution without the magnetic beads.

In the method, a laser beam is irradiated onto a solution containing magnetic beads and the magnetic beads cause an ablation due to the energy of the laser to transfer shock wave, vapor pressure and heat to the cell surface. At this time, physical shocks are also applied to the cell surface. A laser ablation refers to general phenomenon occurred in materials exposed to a laser beam. The laser ablation rapidly raises the temperature of a material surface from several hundred to several thousand degrees. If the temperature of the material surface is raised to the evaporation point or higher, the saturated vapor pressure on the surface rapidly increases according to an evaporation of the liquid phase material.

The magnetic beads heated by the laser raise the temperature of the solution and directly disrupt the cells. The magnetic beads in the solution do not act as a simple heat conductor but apply thermal, mechanical and physical shocks to the cell surface, thereby effectively disrupting the cell surface.

The lysate of disrupted cells or viruses includes compounds which inhibit a PCR. Thus, to effectively perform the PCR, a separate step for removing the PCR inhibitors from the resulting lysate is required, which is not suitable to effectively implement LOC. In the method of the present invention, the magnetic beads with the PCR inhibitors attached thereto are fixed to a cell lysis capillary wall by means of the magnetic force generator so as to facilitate the PCR.

Specifically, the magnetic beads to which PCR inhibitors, such as proteins and cell debris denatured by boiling, are attached are boiled by the energy of a laser. The magnetic beads with the PCR inhibitors attached thereto are attached to a container wall. Thus, a DNA containing solution, which does not contain the magnetic beads, is located at the lower portion of the container and most magnetic beads with the PCR inhibitors attached thereto are attached to a glass wall at the upper portion of the container, thereby readily removing the PCR inhibitors. This phase separation occurs more effectively in a capillary with a limited diameter. A fixed electromagnet or permanent magnet can be used to ensure the fixation of the separated phases and designate fixing regions.

The present invention also relates to a method of continuously performing purification and amplification of nucleic acids using the nucleic acid purification apparatus, the method including: injecting a solution containing cells or viruses to a capillary-shaped container containing magnetic beads; vibrating the magnetic beads; irradiating a laser beam onto the magnetic beads to disrupt the cells or viruses and binding compounds in the resulting cell or virus lysate to the magnetic beads; fixing the magnetic beads, to which the compounds in the cell or virus lysate are bound, to a capillary-shaped container wall by means of a magnetic force generator; and obtaining a solution without the magnetic bead and transferring the resulting solution to an amplification chamber through a channel connecting the container and the amplification chamber to perform amplification.

For the purpose of LOC implementation, it is necessary to continuously perform separation, purification and amplification of the nucleic acids. Thus, when a DNA solution purified by means of magnetic beads is directly transferred to an amplification chamber through a channel connecting a capillary-shaped container and the amplification chamber so as to amplify the nucleic acids, the above purpose can be achieved. The transfer of nucleic acids to the amplification chamber can be performed by a pump using an electric, mechanical force, and the like.

In an embodiment of the present invention, the laser can include a pulse laser or continuous wave (CW) laser.

If the laser power is too low, the laser ablation cannot efficiently occur. The laser power is from 10 mW to 300 W for the CW laser and 1 mJ/pulse to 1 J/pulse for the pulse laser. Preferably, the pulse laser is 32 mJ/pulse to 1 J/pulse and the CW laser has the power from 10 W to 300 W. When the CW is less than 10 mW and the pulse laser is less than 1 mJ/pulse, an energy sufficient to disrupt cells is not transferred. When the CW is greater than 300 W and the pulse laser is greater than 1 J/pulse, DNA is damaged.

In an embodiment of the present invention, the laser should be generated in a specific wavelength range which allows the magnetic beads to absorb the laser. The laser is generated preferably in the wavelength range of 400 nm or more, and more preferably, in the wavelength range from 750 nm to 1300 nm. This is because DNA is denatured or damaged at a wavelength less than 400 nm. The laser can also be generated in one or more wavelength ranges. That is, the laser can have one wavelength or two or more different wavelengths within the above range.

In an embodiment of the present invention, the size of the magnetic beads is preferably from 50 nm to 1,000 μm, and more preferably, from 1 μm to 50 μm. When the size of the magnetic beads is less than 50 nm, physical and mechanical shocks are insufficient to cause cell lysis. When the size of the magnetic beads is greater than 1,000 μm, it is not suitable for LOC. The magnetic beads can also be a mixture of beads with two or more sizes. That is, the magnetic beads can have equal sizes to each other or be a mixture of beads with different sizes.

In an embodiment of the present invention, the container can have a ratio of diameter to length ranging from 1:2 to 1:50 and have a diameter ranging from 1 nm to 5 mm. A phase containing beads is non-specifically bound to a glass wall, which occurs effectively in a capillary with a limited diameter. Thus, if a container has a dimension outside the above range, a phase separation become difficult, thereby resulting in a reduced purification effect.

In an embodiment of the present invention, the container can be selected from the group consisting of polymers, organic materials, silicon, glass and metals. The container can be composed of any material capable of fixing beads.

In an embodiment of the present invention, the magnetic beads can be any material which is magnetized. In particular, the magnetic beads preferably include at least one material selected from the group consisting of ferromagnetic Fe, Ni, Cr and oxides thereof.

In an embodiment of the present invention, the magnetic beads may be polymers, organic materials, silicon or glass coated with a ferromagnetic metal.

In an embodiment of the present invention, the surface of the magnetic bead is preferably negatively charged so that DNA cannot be attached thereto. The negative charge can be $COO^-$. Since DNA is negatively charged, it does not attach to the magnetic bead, which is negatively charged as well, due to a repulsive force. When DNA is attached to the magnetic bead, it is difficult to separate the DNA from the magnetic beads after cells are disrupted, which makes DNA purification more difficult.

In an embodiment of the present invention, the solution can be selected from the group consisting of saliva, urine, blood, serum and cell cultures. The solution can be any solution having nucleic acids, such as animal cells, plant cells, bacteria, viruses, phage and the like.

The present invention will now be described in greater detail with reference to the following examples. The following examples are for illustrative purposes only and are not intended to limit the scope of the invention.

PREPARATION EXAMPLE 1

Cell Lysis System

As illustrated in FIG. 1, HBV prepared as described below (60 μl), serum (30 μl) and micro magnetic beads (30 μl, Dynabeads® M-270 Carboxylic Acid, DYNAL, Norway) were mixed in a capillary. 808 nm, 21.1 W high power laser beam (HLU25F100-808, LIMO, Germany) was applied to the mixture for disrupting cells for a designated time in individual experiments while stirring the capillary by vortexing (see FIG. 1).

PREPARATION EXAMPLE 2

HBV, Primer and PCR

DNA released from the cells was detected using a pair of PCR primers as follows: primer TMP5-F (SEQ ID No: 1); and primer TMP5-R (SEQ ID No: 2). The primer pair was sites corresponding to 2,269-2,387 nucleotides of HBV genome. PCR was performed by 40 cycles (predenaturation at 50° C. for 10 minutes and at 95° C. for 1 minute, denaturation at 95° C. for 5 seconds, and annealing and elongation at 62° C. for 15 seconds) by means of Taq polymerase (Takara, Korea). The amplified DNA was analyzed in Agilent BioAnalyzer 2100 (Agilent Technologies, Palo Alto, Calif.) with a commercially available DNA 500 assay sizing reagent sets.

EXAMPLE 1

Separation of a Magnetic Bead Phase and a DNA Solution Phase

Figure 2:
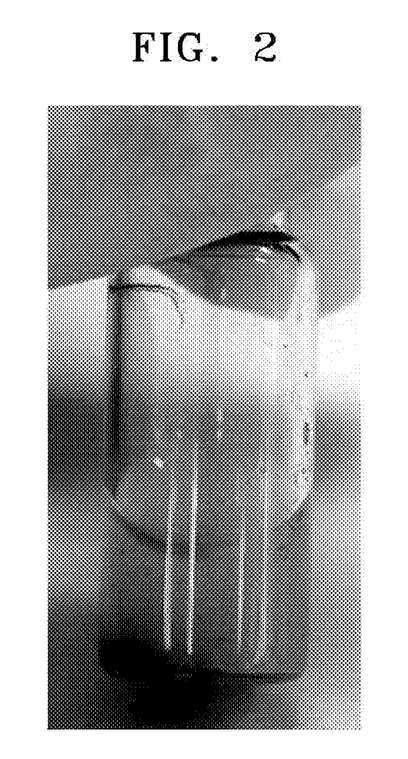
FIG. 2 shows a container with an inner diameter of 9.95 mm, in which a magnetic bead phase and a DNA solution phase are mixed after laser irradiation.

To investigate a degree of phase separation between a magnetic bead phase and a DNA-containing solution phase according to the form of a container, the degree of phase separation was observed using various types of containers. FIG. 2 shows a container with an inner diameter of 9.95 mm, in which a magnetic bead phase and a DNA solution phase are mixed after laser irradiation. Referring to FIG. 2, when the inner diameter of a container is 9.95 mm, magnetic beads with PCR inhibitors, such as denatured proteins and cell debris, bound thereto are not attached to a glass wall and mixed with the DNA containing solution, so that the magnetic bead phase and the DNA containing solution phase are not separated.

Figure 3A:
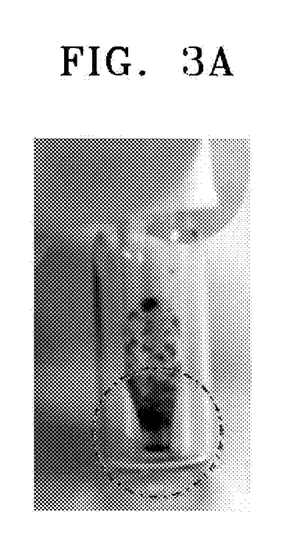
FIG. 3 shows a container with an inner diameter of 4.88 mm, in which a magnetic bead phase and a DNA solution phase are separated after laser irradiation.
Figure 3B:
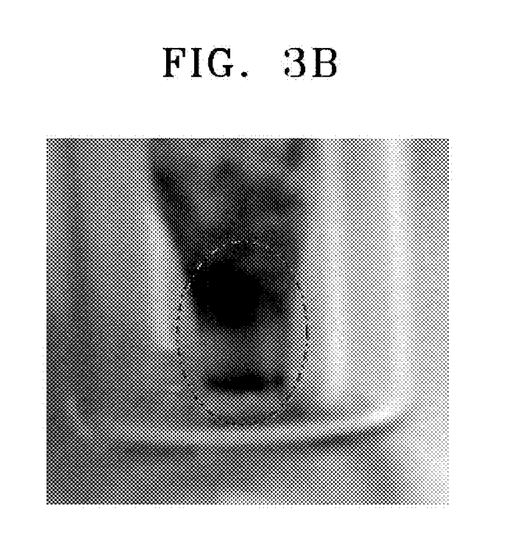

FIG. 3 shows a container with an inner diameter of 4.88 mm, in which a magnetic bead phase and a DNA solution phase are separated after laser irradiation. A in FIG. 3 shows a container in which the magnetic bead phase and the DNA containing solution phase are separated and B in FIG. 3 shows a magnified view of the container shown in A. Referring to FIG. 3, we note that in the case of a capillary with an inner diameter of 4.88 mm, a phase of magnetic beads with PCR inhibitors bound thereto and a DNA containing phase are clearly separated. That is, the magnetic bead containing phase separated is non-specifically bound to a glass wall, which occurs only in a capillary with a diameter of 5 mm or less.

EXAMPLE 2

Binding of PCR Inhibitors to Magnetic Beads

Figure 4:
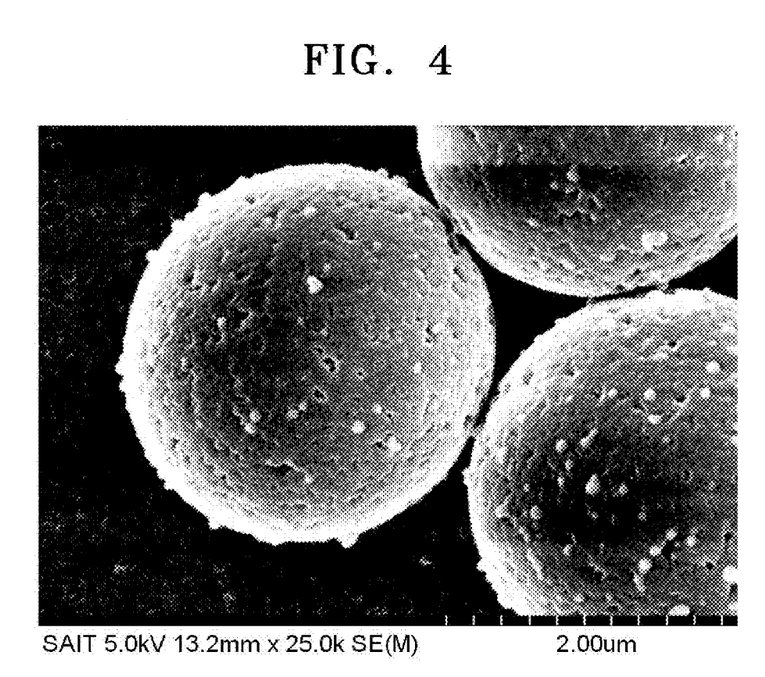
FIG. 4 shows an SEM photograph of Pure Dynabeads® M-270 carboxylic acid.
Figure 5:
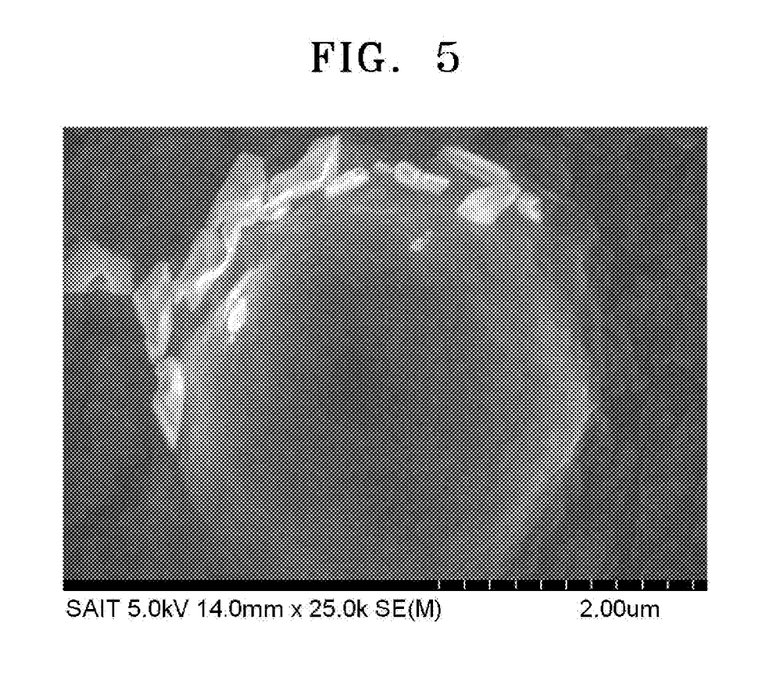
FIG. 5 shows an SEM photograph of Dynabeads® M-270 carboxylic acid attached to glass wall after cell lysis by laser irradiation.
Figure 6:
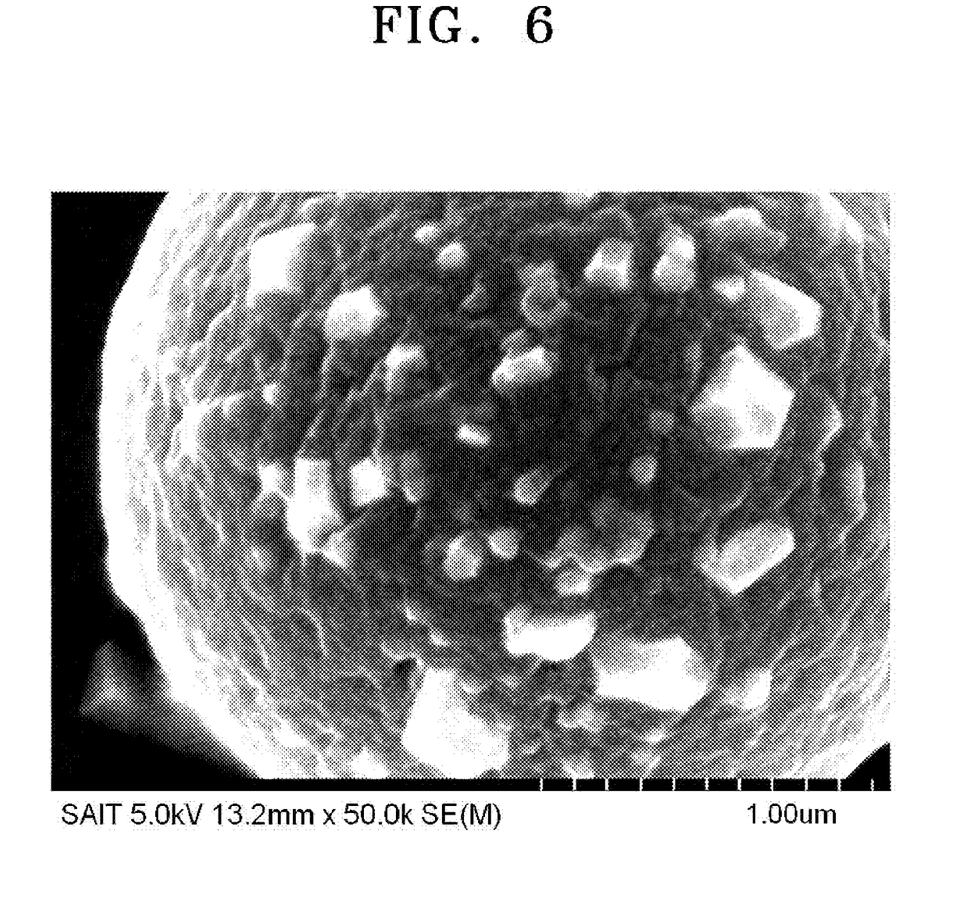
FIG. 6 shows an SEM photograph of Dynabeads® M-270 carboxylic acid taken from the central portion of a glass container after cell lysis by laser irradiation.

To identify whether PCR inhibitors were bound to magnetic beads, an SEM observation was conducted. FIG. 4 shows an SEM photograph of Pure Dynabeads® M-270 carboxylic acid. Pure Dynabeads® M-270 carboxylic acid had a diameter of 2.8 μm±0.2 and the concentration of the beads in a solution was $6 \times 10^7$ beads/30 μl. Referring to FIG. 4, pure magnetic beads had no deposit. In addition, since DNA was negatively charged, it was not attached to the magnetic beads. FIG. 5 shows an SEM photograph of Dynabeads® M-270 carboxylic acid attached to a glass wall after cell lysis by means of laser treatment. As apparent from FIG. 5, many particles were attached to a magnetic bead. The particles were mainly denatured proteins and cell debris, which were primary PCR inhibitors disturbing PCR. FIG. 6 shows an SEM photograph of Dynabeads® M-270 carboxylic acid taken from the central portion of a glass container after cell lysis by means of laser treatment. As apparent from FIG. 6, many particles were attached to a magnetic bead. Thus, denatured proteins and cell debris acting as PCR inhibitors can be readily removed using magnetic beads.

EXAMPLE 3

PCR Amplification Effects According to DNA Purification Methods

Figure 7:
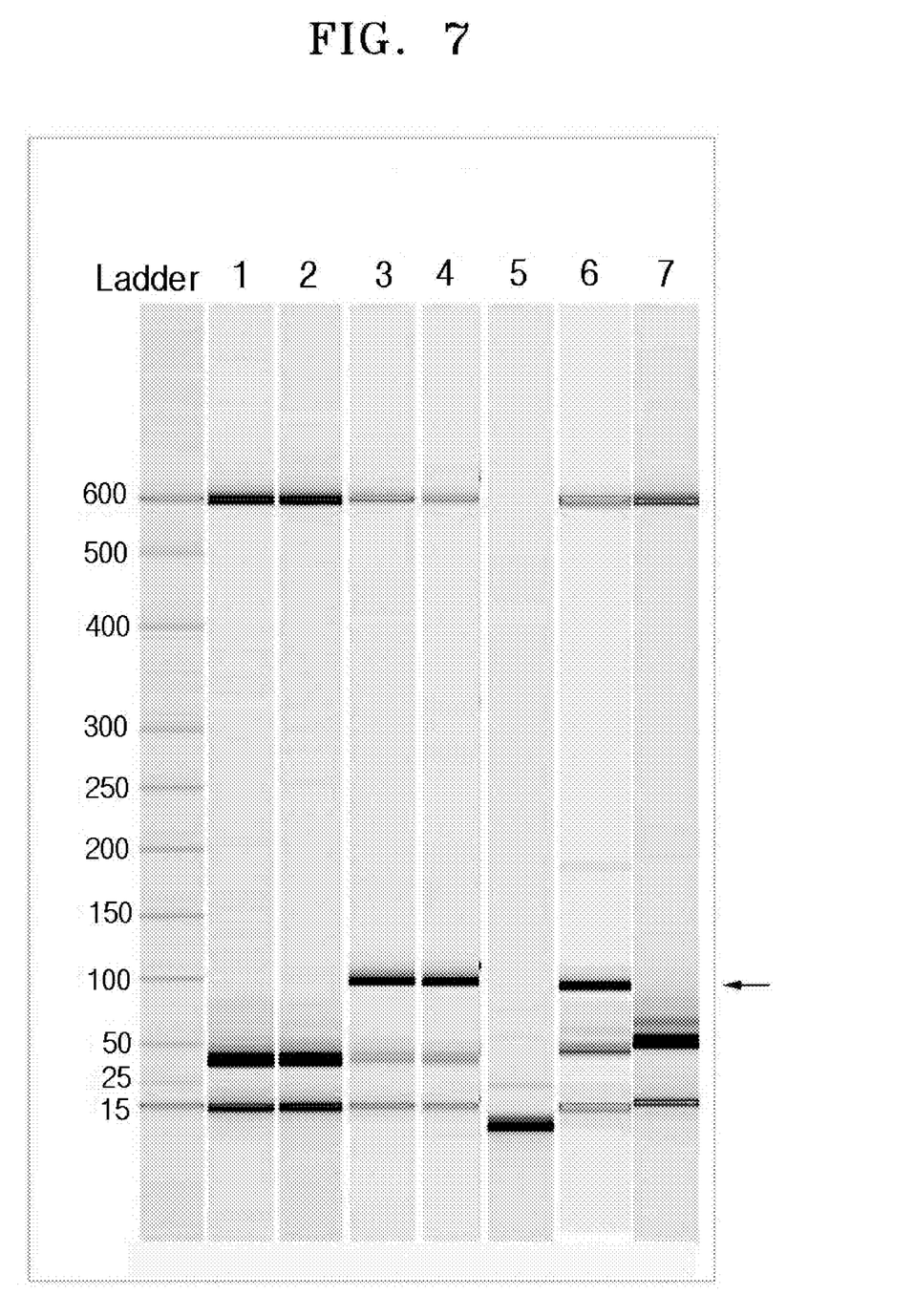
FIG. 7 illustrates the results of electrophoresis of PCR products according to the DNA purification methods.

To study the PCR amplification effects according to the DNA purification methods, cell lysis was performed in a Lightcycler capillary (inner diameter: 2.42 mm, height: 35.40 mm, a ratio of inner diameter:height=1:14.63), and then the PCR was performed using the resulting lysates. FIG. 7 illustrates the results of electrophoresis of the PCR products according to the DNA purification methods. The bands designated by an arrow correspond to the desired PCR products. Lanes 1 and 2 are the results of the PCR performed after 60 and 90 seconds of laser irradiation, respectively, in the absence of the magnetic beads and Lanes 3 and 4 are the results of the PCR performed after 5 and 10 seconds of laser irradiation, respectively, in the presence of the magnetic beads. Lane 5 displays the results of a direct PCR of a recombination HBV (rHBV), lane 6 is a PCR positive control in which a PCR was performed after purifying DNA using Qiagen Ultrasense kit, and lane 7 is a PCR negative control in which a PCR was performed using only distilled water. The respective samples had compositions as given in the following Table.

| Sample | Serum | Bead | rHBV |
|--------|-------|------|------|
| 1 | 50% | — | 50% |
| 2 | 50% | — | 50% |
| 3 | 25% | 25% | 50% |
| 4 | 25% | 25% | 50% |
| 5 | — | — | 100% |
| 6 | 50% | — | 50% |
| 7 | | Distilled water | |

As apparent from FIG. 7, when only laser irradiation was performed without the magnetic beads (lanes 1 and 2), a PCR product was not observed and when a direct PCR of rHBV was performed (lane 5), a PCR product was not observed. However, in the case of the present invention, i.e., when laser irradiation was performed in the presence of the magnetic beads (lanes 3 and 4), PCR products were observed in desired positions. When a PCR was performed after purifying DNA by means of Qiagen Ultrasense kit (lane 6), the desired PCR product was observed. As apparent from these results, the method of the present invention shows a PCR efficiency similar to the case that DNA is purified by means of Qiagen Ultrasense kit as a positive control, which requires considerable time and many steps for purification. Thus, the method of the present invention can be effectively applied to LOC since a PCR is efficiently performed without a separate DNA purification step.

Figure 8:
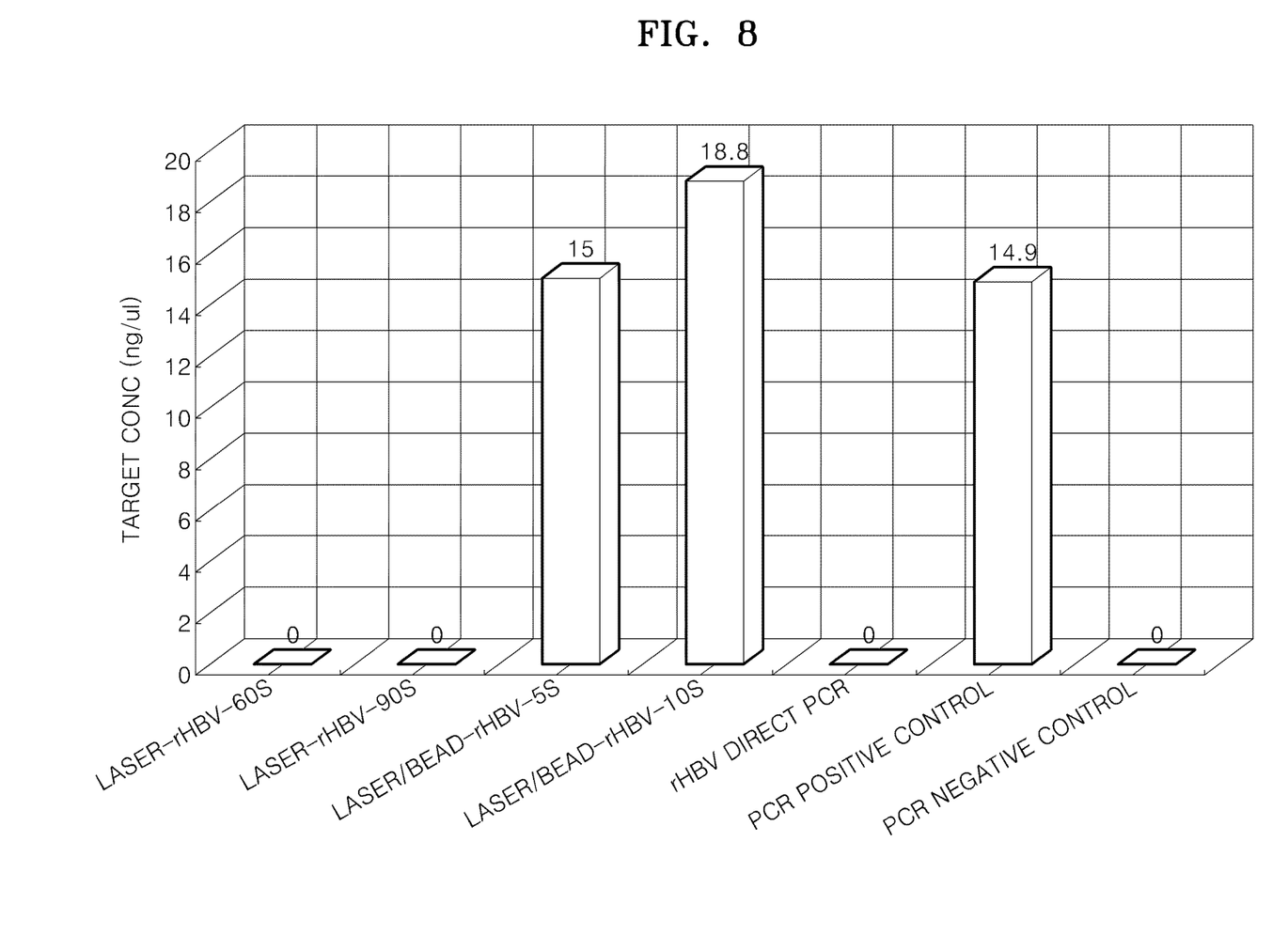
FIG. 8 illustrates the concentration of an amplified PCR product.

FIG. 8 illustrates the concentrations of amplified PCR products. The bars represent the concentration (ng/µl) of the amplified DNA. The amount of the PCR product was quantified by means of Agilent BioAnalyzer 2100. As apparent from FIG. 8, the PCR results using the method of the present invention are similar to or superior to the PCR results using Qiagen Ultrasense kit. Thus, according to the method of the present invention, the PCR for the DNA analysis can be readily performed without a separate purification process.

EXAMPLE 4

Figure 9:
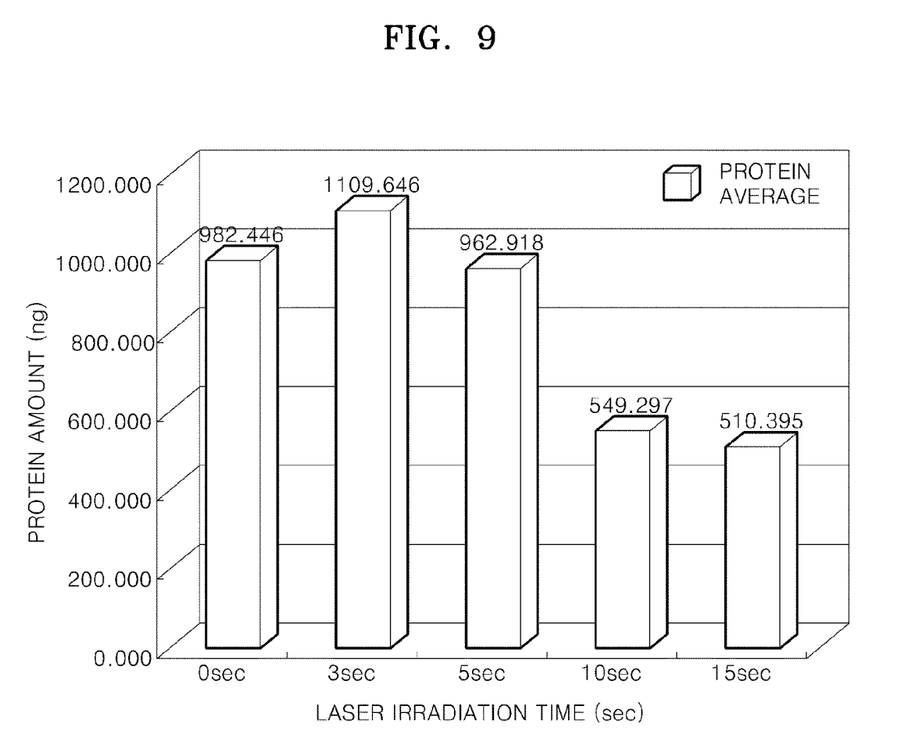
FIG. 9 illustrates the amount of proteins in a cell lysate according to laser irradiation time.

Comparison of the Amount of Proteins in a Solution According to Laser Irradiation Time To study the amount of proteins adsorbed by the magnetic beads after cell lysis, the amount of proteins in the cell lysate was investigated according to laser irradiation time. The amount of proteins in the resulting cell lysate after cell lysis was measured using a CBQCA protein quantification kit (C-6667, Molecular Probes, see the preparation manual). FIG. 9 shows the amount of proteins in a cell lysate according to laser irradiation time. Referring to FIG. 9, the amount of proteins in the cell lysate was significantly reduced at laser irradiation times of 10 and 15 seconds. The significant reduction of the amount of proteins in the cell lysate at a laser irradiation time of 10 seconds indicates that the PCR amplification is efficiently performed, which is consistent with the results of FIGS. 7 and 8.

As described above, according to the method of the present invention, a PCR yield can be increased since PCR inhibitors can be readily removed by means of a phase separation in a capillary. The use of an electromagnet ensures the removal of the PCR inhibitors. In addition, since cell lysis and DNA purification process can be simultaneously performed, LOC steps can be reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of purifying nucleic acids from cells or viruses comprising:
   - injecting a solution containing cells or viruses to a capillary-shaped container containing magnetic beads, wherein the container has a diameter ranging from 1 mm to 5 mm and a ratio of diameter to length ranging from 1:2 to 1:50, and wherein the size of the magnetic beads is from 50 nm to about 50 µm;
   - vibrating the magnetic beads;
   - irradiating a laser beam onto the magnetic beads to disrupt the cells or viruses and binding proteins and cell debris in the resulting cell or virus lysate to the magnetic beads;
   - fixing the magnetic beads, to which the proteins and cell debris are bound, to a wall of the capillary-shaped container by means of a magnetic force generator; and
   - obtaining a nucleic acid-containing solution without the magnetic beads.

2. The method of claim 1, wherein the laser comprises a pulse laser or continuous wave (CW) laser.

3. The method of claim 2, wherein the pulse laser is 1 mJ/pulse or more and the CW laser has a power of 10 mW or more.

4. The method of claim 3, wherein the pulse laser is 32 mJ/pulse or more and the CW laser has a power of 10 W or more.

5. The method of claim 1, wherein the laser beam is generated in a wavelength range of 400 nm or more.

6. The method of claim 5, wherein the laser beam is generated in a wavelength range of from 750 nm to 1300 nm.

7. The method of claim 5, wherein the laser is generated in one or more wavelength ranges.

8. The method of claim 1, wherein the magnetic beads is a mixture of beads having two or more sizes.

9. The method of claim 1, wherein the container is selected from the group consisting of polymers, organic materials, silicon, glass and metals.

10. The method of claim 1, wherein the magnetic beads comprise at least one material selected from the group consisting of ferromagnetic Fe, Ni, Cr, and oxides thereof.

11. The method of claim 1, wherein the magnetic beads are polymers, organic materials, silicon or glass coated with a ferromagnetic metal.

12. The method of claim 1, wherein the magnetic beads have a negatively charged surface.

13. The method of claim 1, wherein the solution is selected from the group consisting of saliva, urine, blood, serum and cell cultures.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: forward primer

<400> SEQUENCE: 1
agtgtggatt cgcactcct                                             19

```
<210> SEQ ID NO 2
<211> LENGTH: 23
<212> TYPE: DNA
<213> ORGANISM: Artificial
<220> FEATURE:
<223> OTHER INFORMATION: reverse primer

<400> SEQUENCE: 2
gagttcttct tctaggggac ctg                                              23
```